United States Patent
Maes et al.

(10) Patent No.: US 10,055,536 B2
(45) Date of Patent: Aug. 21, 2018

(54) SYSTEMS AND METHODS FOR FORMING AND UTILIZING BENDING MAPS FOR OBJECT DESIGN

(71) Applicant: Materialise N.V., Leuven (BE)

(72) Inventors: Jan Maes, Herselt (BE); Mohd Azman Mohd Ismail, Kuala Lumpur (MY); Tom Cluckers, Kuringen (BE)

(73) Assignee: Materialise, NV, Leuven (BE)

( * ) Notice: Subject to any disclaimer, the term of this patent is extended or adjusted under 35 U.S.C. 154(b) by 578 days.

(21) Appl. No.: 14/609,322

(22) Filed: Jan. 29, 2015

(65) Prior Publication Data

US 2015/0149126 A1 May 28, 2015

Related U.S. Application Data

(63) Continuation of application No. PCT/EP2013/065935, filed on Jul. 29, 2013.

(60) Provisional application No. 61/677,378, filed on Jul. 30, 2012.

(51) Int. Cl.
| | | |
|---|---|---|
| G06F 17/50 | (2006.01) | |
| G06T 19/20 | (2011.01) | |
| A61B 17/80 | (2006.01) | |
| A61B 17/00 | (2006.01) | |
| A61B 34/10 | (2016.01) | |
| B29C 64/112 | (2017.01) | |

(52) U.S. Cl.
CPC ...... G06F 17/5086 (2013.01); A61B 17/8085 (2013.01); G06T 19/20 (2013.01); A61B 2017/00526 (2013.01); A61B 2034/108 (2016.02); B29C 64/112 (2017.08); G06T 2219/2021 (2013.01)

(58) Field of Classification Search
CPC ............ G06F 17/5086; A61B 17/8085; A61B 2034/108; A61B 2017/00526; G06T 19/20; G06T 2219/2021; B29C 67/0059
USPC .......................................................... 703/1
See application file for complete search history.

(56) References Cited

U.S. PATENT DOCUMENTS

| | | | |
|---|---|---|---|
| 2003/0056561 A1 | 3/2003 | Butscher et al. | |
| 2008/0309664 A1 | 12/2008 | Zhou et al. | |
| 2009/0149977 A1 | 6/2009 | Schendel | |

FOREIGN PATENT DOCUMENTS

| | | | |
|---|---|---|---|
| WO | 2012027185 A1 | 3/2012 | |
| WO | WO 2012027185 A1 * | 3/2012 | ............ G06T 19/20 |

OTHER PUBLICATIONS

Von Jan et al. "Computer Assisted Orthopaedic Surgery"; International Journal of Computer Assisted Radiology and Surgery; A Journal for Interdisciplinary Research, Development and Applications of Image Guided Diagnosis and Therapy, Springer, Berlin, DE, vol. 1, No. 7, Jun. 1, 2006, pp. 229-250.

Lazarus et al. "Axial deformations: an intuitive deformation technique"; Computer Aided Design, Elsevier Publishers BV., Barking, GB, vol. 26, No. 8, Aug. 1, 1994, pp. 607-613.

(Continued)

*Primary Examiner* — Saif A Alhija
(74) *Attorney, Agent, or Firm* — Patterson & Sheridan LLP

(57) ABSTRACT

Systems and methods for designing digital representations of 3-D objects and manufacturing such objects are disclosed herein. In some aspects, the systems and methods described relate to bending maps that define regions on a physical object that can be bent or manipulated in order to design the 3-D object.

20 Claims, 13 Drawing Sheets

(56) References Cited

OTHER PUBLICATIONS

Popa et al. "Material-Aware Mesh Deformations"; Shape Modeling and Applications, 2006. SMI 2006. IEEE International Co nference on Matsushima, Japan Jun. 14-16, 2006, Piscataway, NJ, USA,IEEE, Jun. 14, 2006, pp. 1-12.
Bou-Sleiman et al. "Minimization of Intra-Operative Shaping of Orthopaedic Fixation Plates: A Population-Based Design" Medical Image Computing and Computer-Assisted Intervention A MICCAI 2011, Springer Berlin Heidelberg, Berlin, Heidelberg, Sep. 18, 2011, pp. 409-416.
Sagbo et al. "Design and implementation of deformation algorithms for computer assisted orthopedic surgery: application to virtual implant database and preliminary results"; Engineering in Medicine and Biology Society, 2005. IEEE-EMBS 2005. 27th Annual International Conference of the Shanghai, China Sep. 1-4, 2005, Piscataway, NJ, USA, Jan. 1, 2005, pp. 6946-6949.
Olszewski et al. "Towards an intergrated system for planning and assisting maxillofacial orthognathic surgery"; Computer Methods and Programs in Biomedicine, Elsevier, Amsterdam, NL, vol. 91, No. 1, Jul. 1, 2008, pp. 13-21.
International Search Report and Written Opinion dated Jan. 8, 2014 on related Application PCT/EP2013/065935 filed Jul. 29, 2013.

\* cited by examiner

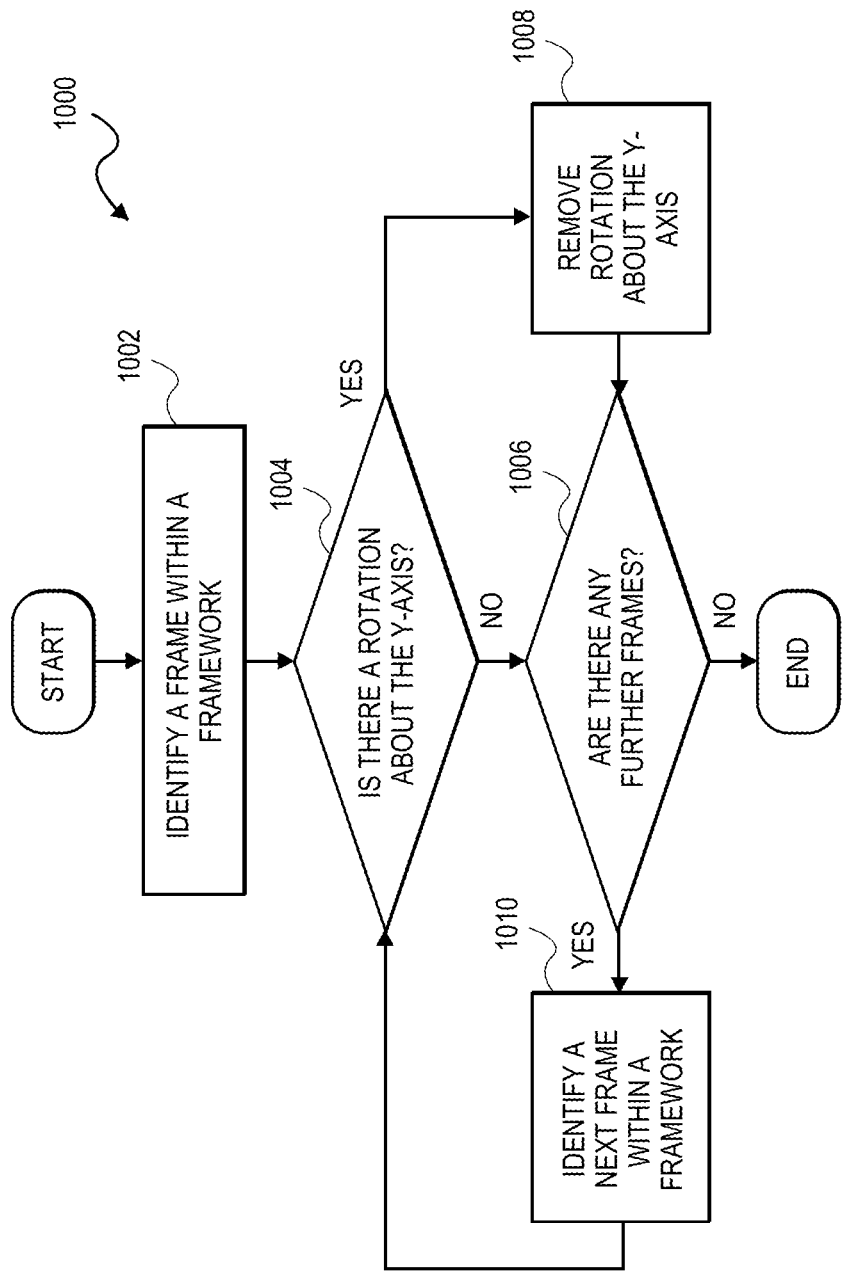

SYSTEMS AND METHODS FOR FORMING AND UTILIZING BENDING MAPS FOR OBJECT DESIGN

CROSS-REFERENCE TO RELATED APPLICATIONS

This application is a continuation under 35 U.S.C. § 120 of International Application No. PCT/EP2013/065935, filed Jul. 29, 2013 (published by the International Bureau as International Publication No. WO/2014/019998 on Feb. 6, 2014), which claims priority to U.S. Provisional Patent Application No. 61/677,378, filed Jul. 30, 2012. The entire contents of each of the above-referenced applications are hereby incorporated by reference.

BACKGROUND OF THE INVENTION

Field of the Invention

This invention relates to systems and methods for modeling objects on a computer. More particularly, the invention relates to forming and utilizing bending maps for object design, wherein the object may later be made through additive manufacturing.

Description of the Related Technology

Object design and manufacturing of objects are used to create necessary tools for a number of different industries. For example, parts, tools, etc. may be designed and manufactured for use in all aspects of everyday life. The process of designing and manufacturing such objects, however, can be time intensive and expensive. For example, traditional manufacturing techniques may require a prototype be designed and built, molds created based on the design, drilling and cutting of components, and other time consuming and expensive techniques to create a single object. There may be economies of scale when making subsequent objects identical to the initially designed object as molds, etc. can be reused. However, for one off objects, no such economies of scale are gained.

Accordingly, traditional manufacturing techniques are ill suited for generating one off or customized objects, such as, surgical implants specifically designed for a patient, prototypes, etc. Processes such as additive manufacturing (e.g., 3D printing), can overcome such limitations by reducing the time and cost of creating an object.

Additive manufacturing can be defined as a group of techniques used to fabricate a tangible model of an object typically using three-dimensional (3-D) computer aided design (CAD) data of the object. Currently, a multitude of Additive Manufacturing techniques is available, including stereolithography, Selective Laser Sintering, Fused Deposition Modeling, foil-based techniques, etc.

Selective laser sintering uses a high power laser or another focused heat source to sinter or weld small particles of plastic, metal, or ceramic powders into a mass representing the 3-dimensional object to be formed.

Fused deposition modeling and related techniques make use of a temporary transition from a solid material to a liquid state, usually due to heating. The material is driven through an extrusion nozzle in a controlled way and deposited in the required place as described among others in U.S. Pat. No. 5,141,680.

Foil-based techniques fix coats to one another by means of gluing or photo polymerization or other techniques and cut the object from these coats or polymerize the object. Such a technique is described in U.S. Pat. No. 5,192,539.

Typically additive manufacturing techniques start from a digital representation of the 3-D object to be formed. Generally, the digital representation is sliced into a series of cross-sectional layers which can be overlaid to form the object as a whole. The additive manufacturing apparatus uses this data for building the object on a layer-by-layer basis. The cross-sectional data representing the layer data of the 3-D object may be generated using a computer system and computer aided design and manufacturing (CAD/CAM) software. Traditional CAD/CAM software may require significant skill to properly design a 3-D object and can require time consuming techniques and computations to generate the digital representation of the 3-D object. Accordingly, improved systems and techniques are needed for generating the digital representation of the 3-D object.

SUMMARY

Various implementations of systems, methods and devices within the scope of the appended claims each have several aspects, no single one of which is solely responsible for the desirable attributes described herein. Without limiting the scope of the appended claims, some prominent features are described herein.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

One aspect of the subject matter described in the disclosure provides an apparatus for generating a framework to guide manipulation of a physical object. The apparatus includes a processor configured to generate a framework based on a physical object, the framework comprising one or more frames that define one or more regions on the physical object for manipulation. The processor is further configured to generate one or more constraints for at least one of the one or more regions, the one or more constraints comprising limitations on manipulations applied to the one or more regions based on physical properties of the physical object. The processor is further configured to generate a model of the physical object based on the framework and the one or more constraints.

Another aspect of the subject matter described in the disclosure provides an implementation of a method of generating a framework to guide manipulation of a physical object. The method includes generating a framework based on a physical object, the framework comprising one or more frames that define one or more regions on the physical object for manipulation. The method further includes generating one or more constraints for at least one of the one or more regions, the one or more constraints comprising limitations on manipulations applied to the one or more regions based on physical properties of the physical object. The method further includes generating a model of the physical object based on the framework and the one or more constraints.

Yet another aspect of the subject matter described in the disclosure provides an apparatus for generating a framework to guide manipulation of a physical object. The apparatus includes means for generating a framework based on a physical object, the framework comprising one or more frames that define one or more regions on the physical object for manipulation. The apparatus further includes means for generating one or more constraints for at least one of the one or more regions, the one or more constraints comprising limitations on manipulations applied to the one or more regions based on physical properties of the physical object. The apparatus further includes means for generating a model of the physical object based on the framework and the one or more constraints.

BRIEF DESCRIPTION OF THE DRAWINGS

FIG. 10 illustrates an exemplary process for achieving an in-plane rotated framework.

DETAILED DESCRIPTION OF CERTAIN INVENTIVE EMBODIMENTS

The following detailed description is directed to certain specific embodiments. However, the teachings herein can be applied in a multitude of different ways. In this description, reference is made to the drawings wherein like parts are designated with like numerals throughout.

The present invention will be described with respect to particular embodiments but the invention is not limited thereto but only by the claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of when referring to recited components, elements or method steps also include embodiments which "consist of said recited components, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the features of the claimed embodiments can be used in any combination.

Figure 1:
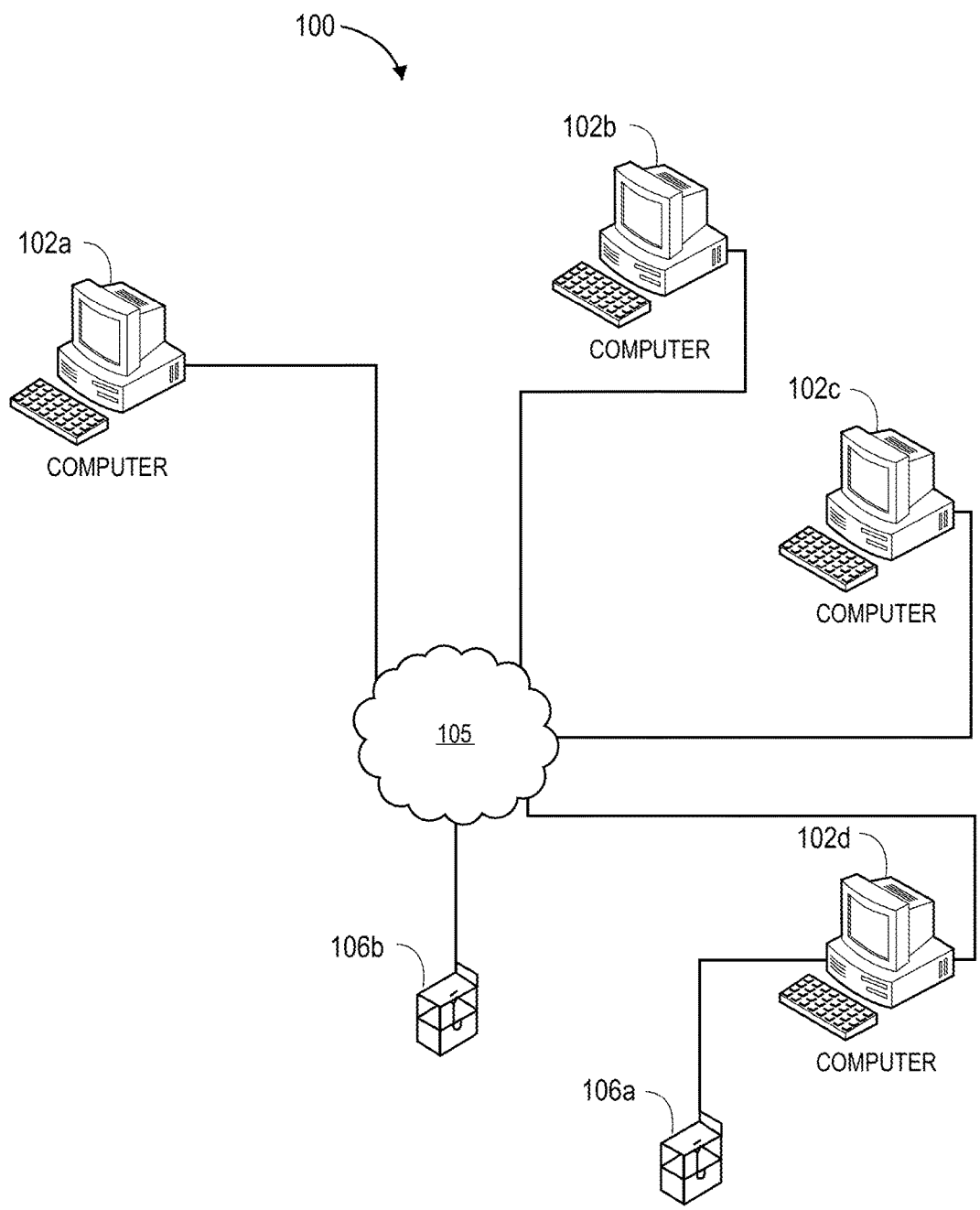
FIG. 1 depicts one example of a system for designing and manufacturing 3-D objects.

FIG. 1 depicts one example of a system 100 for designing and manufacturing 3-D objects. The system 100 is configured to support the techniques described herein. The system 100 includes one or more computers 102a-102d, which can be, for example, any workstation, server, or other computing device capable of processing information. In some aspects, each of the computers 102a-102d can be connected, by any suitable communications technology (e.g., an internet protocol), to a network 105 (e.g., the Internet). Accordingly, the computers 102a-102d may transmit and receive information (e.g., software, digital representations of 3-D objects, commands or instructions to operate an additive manufacturing device, etc.) between each other via the network 105. The system 100 further includes one or more additive manufacturing devices (e.g., 3-D printers) 106a-106b. As shown the additive manufacturing device 106a is directly connected to a computer 102d (and through computer 102d connected to computers 102a-102c via the network 105) and additive manufacturing device 106b is connected to the computers 102a-102d via the network 105. Accordingly, one of skill in the art will understand that an additive manufacturing device 106 may be directly connected to a computer 102, connected to a computer 102 via a network 105, and/or connected to a computer 102 via another computer 102 and the network 105.

It should be noted that though the system 100 is described with respect to a network and one or more computers, the techniques described herein also apply to a single computer 102, which may be directly connected to an additive manufacturing device 106.

Figure 2:
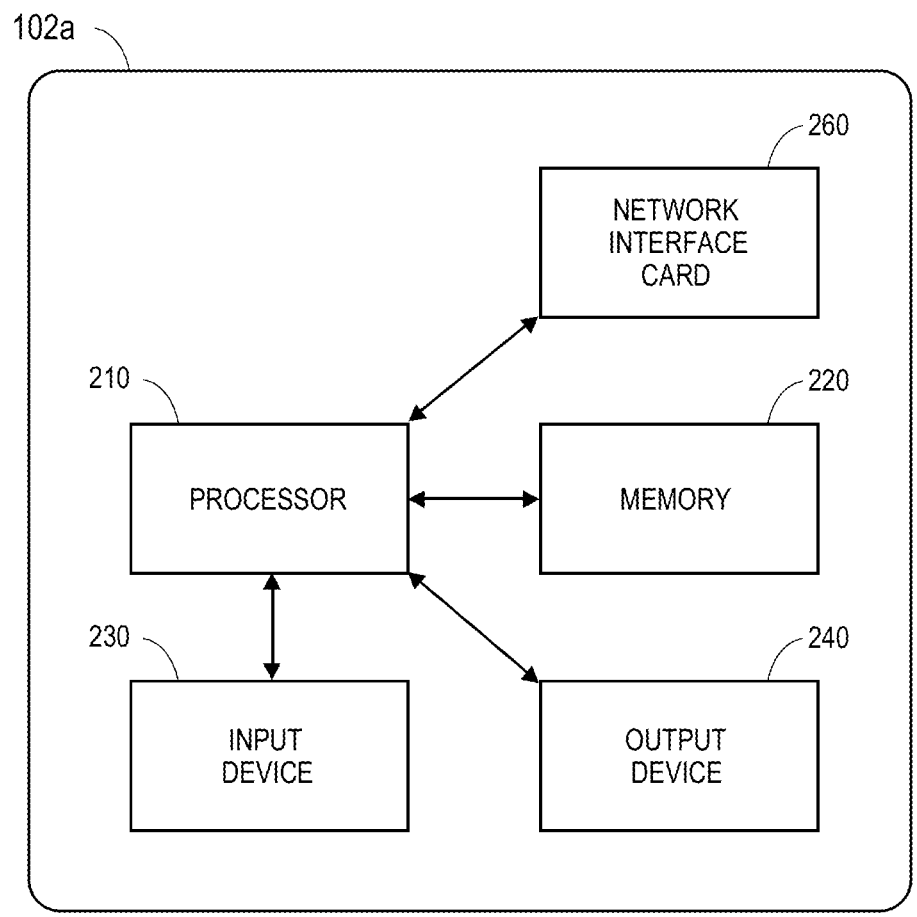
FIG. 2 illustrates a functional block diagram of one example of a computer of FIG. 1.

FIG. 2 illustrates a functional block diagram of one example of a computer of FIG. 1. The computer 102a includes a processor 210 in data communication with a memory 220, an input device 230, and an output device 240. In some embodiments, the processor is further in data communication with an optional network interface card 260. Although described separately, it is to be appreciated that functional blocks described with respect to the computer 102a need not be separate structural elements. For example, the processor 210 and memory 220 may be embodied in a single chip.

The processor 210 can be a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein. A processor may also be implemented as a combination of computing devices, e.g., a combination of a DSP and a microprocessor, a plurality of microprocessors, one or more microprocessors in conjunction with a DSP core, or any other such configuration.

The processor 210 can be coupled, via one or more buses, to read information from or write information to memory 220. The processor may additionally, or in the alternative, contain memory, such as processor registers. The memory 220 can include processor cache, including a multi-level hierarchical cache in which different levels have different capacities and access speeds. The memory 220 can also include random access memory (RAM), other volatile storage devices, or non-volatile storage devices. The storage can include hard drives, optical discs, such as compact discs (CDs) or digital video discs (DVDs), flash memory, floppy discs, magnetic tape, and Zip drives.

The processor 210 also may be coupled to an input device 230 and an output device 240 for, respectively, receiving input from and providing output to a user of the computer 102a. Suitable input devices include, but are not limited to, a keyboard, buttons, keys, switches, a pointing device, a mouse, a joystick, a remote control, an infrared detector, a bar code reader, a scanner, a video camera (possibly coupled with video processing software to, e.g., detect hand gestures or facial gestures), a motion detector, or a microphone (possibly coupled to audio processing software to, e.g., detect voice commands). Suitable output devices include, but are not limited to, visual output devices, including displays and printers, audio output devices, including speakers, headphones, earphones, and alarms, additive manufacturing devices, and haptic output devices.

The processor 210 further may be coupled to a network interface card 260. The network interface card 260 prepares data generated by the processor 210 for transmission via a network according to one or more data transmission protocols. The network interface card 260 also decodes data received via a network according to one or more data transmission protocols. The network interface card 260 can include a transmitter, receiver, or both. In other embodiments, the transmitter and receiver can be two separate components. The network interface card 260, can be embodied as a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein.

Figure 3:
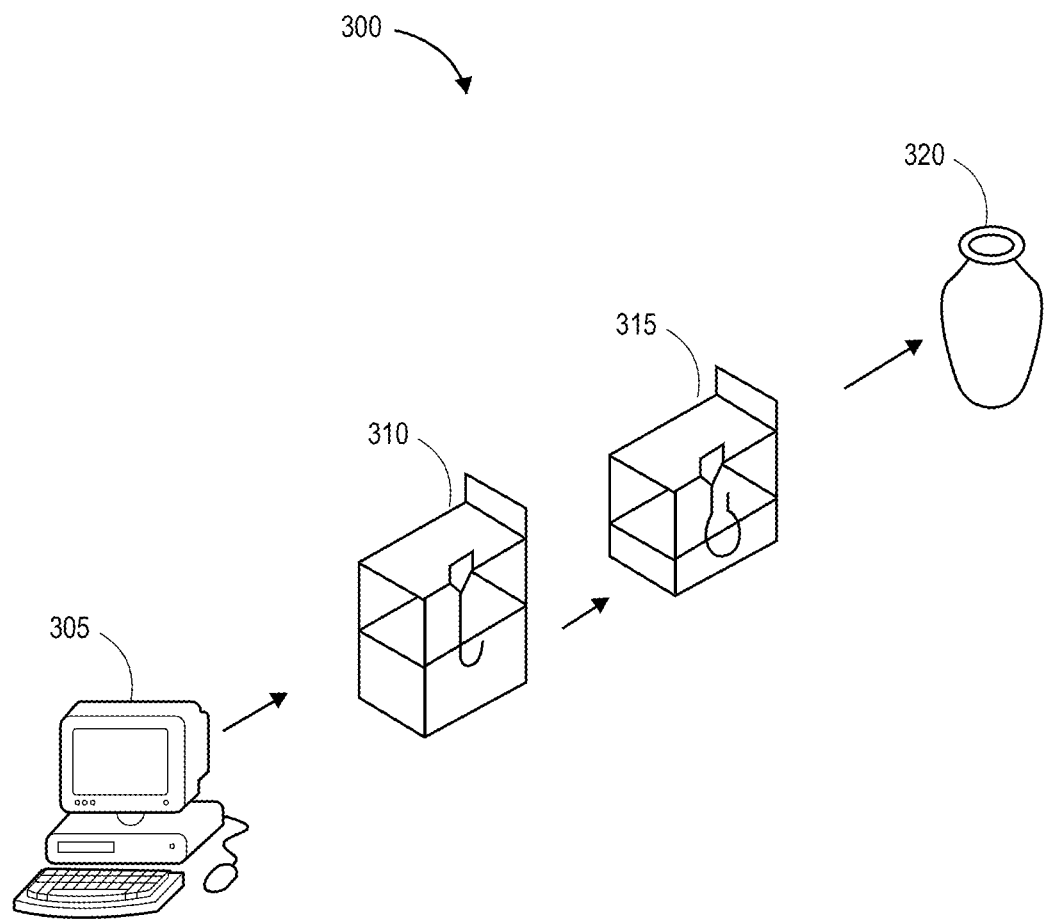
FIG. 3 illustrates a process for manufacturing a 3-D object.

FIG. 3 illustrates a process 300 for manufacturing a 3-D object. As shown, at a step 305, a digital representation of the 3-D object is designed using a computer, such as the computer 102a. Continuing at a step 310, information is sent from the computer 102a to an additive manufacturing device, such as additive manufacturing device 106. At a step 315, the additive manufacturing device 106 begins manufacturing the 3-D object using suitable materials. Suitable materials include, but are not limited to polyurethane, acrylonitrile butadiene styrene (ABS), polycarbonate (PC), PC-ABS, polyamide, polyamide with additives such as glass or metal particles, methyl methacrylate-acrylonitrile-butadiene-styrene copolymer, resorbable materials such as polymer-ceramic composites, etc. Examples of commercially available materials are: DSM Somos® series of materials 7100, 8100, 9100, 9420, 10100, 11100, 12110, 14120 and 15100 from DSM Somos; ABSplus-P430, ABSi, ABS-ESD7, ABS-M30, ABS-M30i, PC-ABS, PC-ISO, PC, ULTEM 9085, PPSF and PPSU materials from Stratasys; Accura Plastic, DuraForm, CastForm, Laserform and VisiJet line of materials from 3-Systems; Aluminium, Cobalt-Chrome and Stainless Steel materials; Maranging Steel; Nickel Alloy; Titanium; the PA line of materials, PrimeCast and PrimePart materials and Alumide and CarbonMide from EOS GmbH. Further, at a step 320, the 3-D object is completed.

Figure 4:
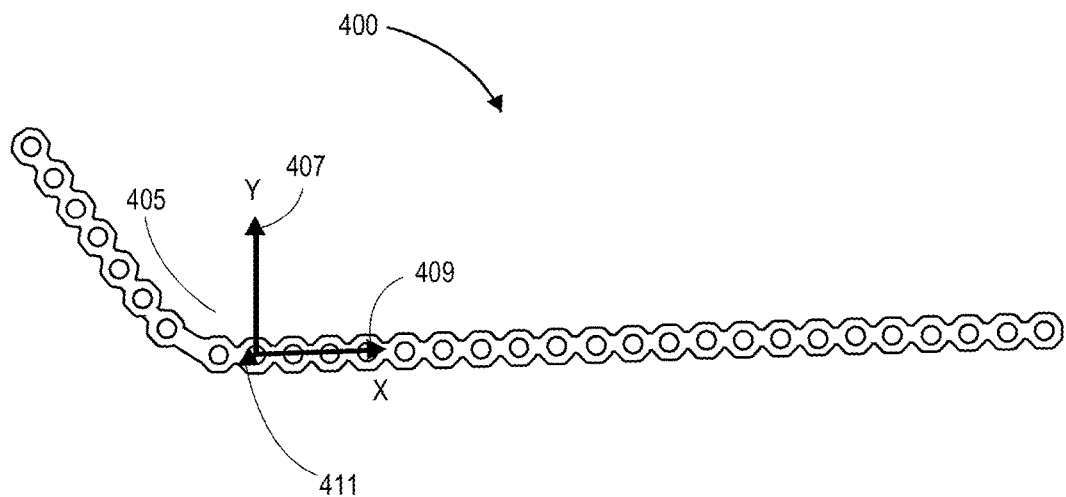
FIG. 4 illustrates an image of a digital representation of a 3-D object as may be viewed on a computer.

According to certain aspects, systems and methods allow for forming and utilizing bending maps in order to generate and/or design digital representations of 3-D objects. FIG. 4 illustrates how an image of a digital representation of a 3-D object 400 may be viewed on the computer 102a. The computer 102a may store data that defines the digital representation of the 3-D object 400 and further comprise software (e.g., CAD/CAM software, etc.) configured to render the image of the 3-D object 400 for output, such as a computer screen or monitor. Also shown in FIG. 4, is a representation of a "frame" 405. In some embodiments, a "frame" defines one or more regions on a 3-D object that can be manipulated according to certain parameters and/or constraints. The frame may be defined at a specific location on the 3-D object, such as according to a set of coordinates of any suitable coordinate system. The frame may define one or more axes about which to rotate or manipulate a model of the 3-D object, such as the x-y-z axes of a Cartesian coordinate system as discussed in further detail below. For example, coordinate 407 is oriented along a y-axis, coordinate 409 is oriented along the x-axis, and coordinate 411 is oriented along the z-axis. As would be understood by one of skill in the art, the axes may be defined to be oriented in any way on the frame. The locations where frames are defined on a 3-D object may be based on one or more factors such as the following: physical constraints of a 3-D object (e.g., it may be difficult to manipulate or bend objects in certain sections), application of the 3-D object (e.g., certain applications, such as surgery, may require a tool be manipulated or bent in precise locations), materials used to create the 3-D object (e.g., certain materials may be capable of only a certain degree or location of manipulation without compromising the integrity of the 3-D object).

In some embodiments, for a given 3-D object, a plurality of frames is defined. The plurality of frames may be referred to as a "framework." For a substantially linear object, such as shown in FIG. 4, the framework may comprise a series of frames along the length of the object that may be referred to as a "frame list." For non-linear objects, such as a rectangular plate, the framework may comprise frames placed along a plane in two dimensions and be referred to as a "frame grid."

Figure 5:
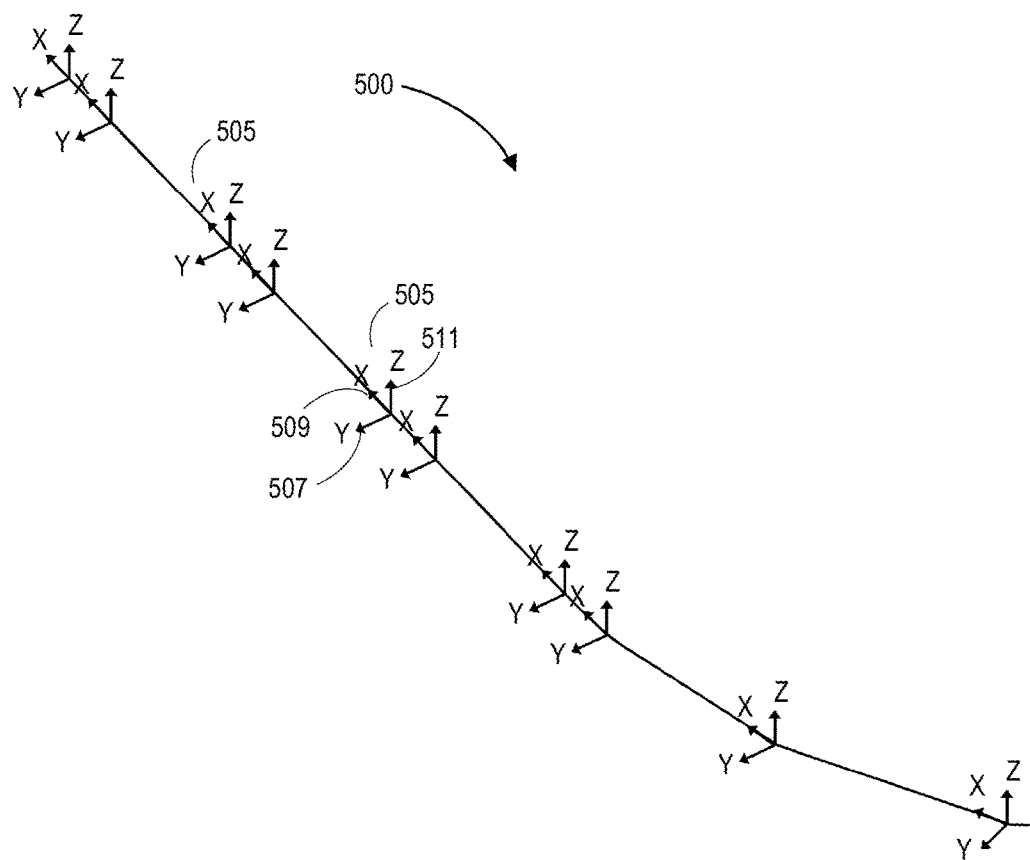
FIG. 5 illustrates an example of a framework of a 3-D object.
Figure 6:
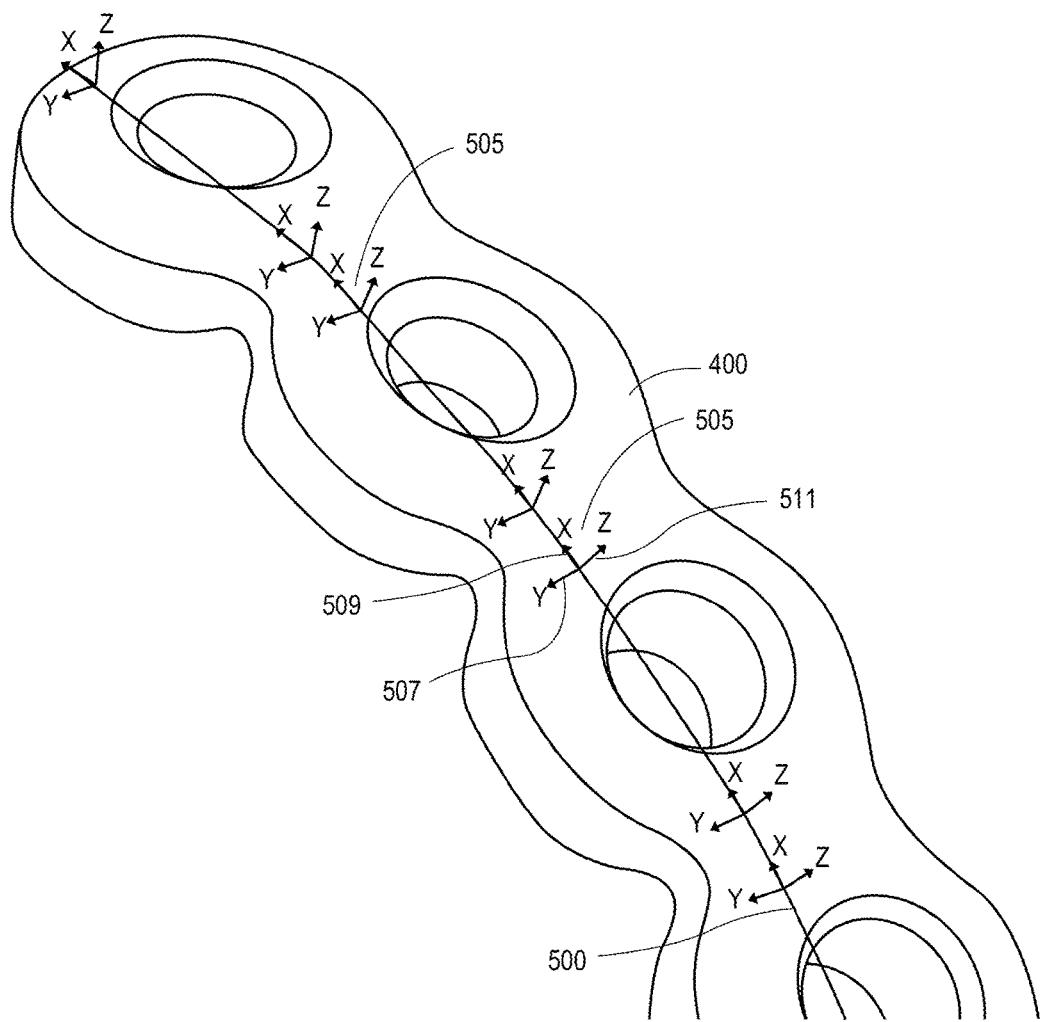
FIG. 6 illustrates the framework of FIG. 5 aligned with the 3-D object of FIG. 4.

FIG. 5 illustrates an example of framework 500 of a 3-D object. The framework 500, as shown, comprises a plurality of frames 505. The framework 500 may correspond to the 3-D object 400. For example, each frame 505 of the framework 500 may correspond to a particular location or region on the 3-D object 400. Each frame 505 may be positioned along the framework 500 at a particular location or region based on parameters or properties of the 3-D object for which the framework 500 corresponds (e.g., physical constraints, application of the 3-D object, material, shape, etc.). FIG. 6 illustrates an example of the framework 500 aligned with the 3-D object 400. As shown in FIG. 6, each frame 505 aligns with a specific location on the 3-D object 400. Accordingly, a framework, such as the framework 500, can act as a model or representation of a 3-D object, such as the 3-D object 400.

The frames 505 may define how the 3-D object 400 can be manipulated at the location of each frame 505. In some embodiments, each frame 505 defines one or more axes, e.g., axes of a Cartesian coordinate system. For example, as shown in FIGS. 5-6, each frame 505 defines an x-axis 509, a y-axis 507, and a z-axis 511. Further, the frame 505 may define a degree of rotation to be applied to the 3-D object 400 about each of the axes. In some embodiments, the degree of rotation to be applied to a frame is constrained based on one or more physical properties of the 3-D object (e.g., material, shape, etc.). For example, rotating/bending/manipulating a 3-D object at a particular location may compromise the integrity of the 3-D object if performed past a threshold, therefore rotating/bending/manipulating may be constrained from being performed beyond the threshold. As another example, rotating/bending/manipulating a 3-D object at a particular location may be undesirable or impossible, therefore constraints for particular locations may be defined where rotating/bending/manipulating is constrained from being performed at all. In some embodiments, the rotation about each of the axes is performed incrementally. For example, each frame 505 of the framework 500 may be rotated about a single axis at a time, such as first rotating about the x-axis 509, next rotating about the y-axis 507, and lastly rotating about the z-axis 511.

Figure 7A:
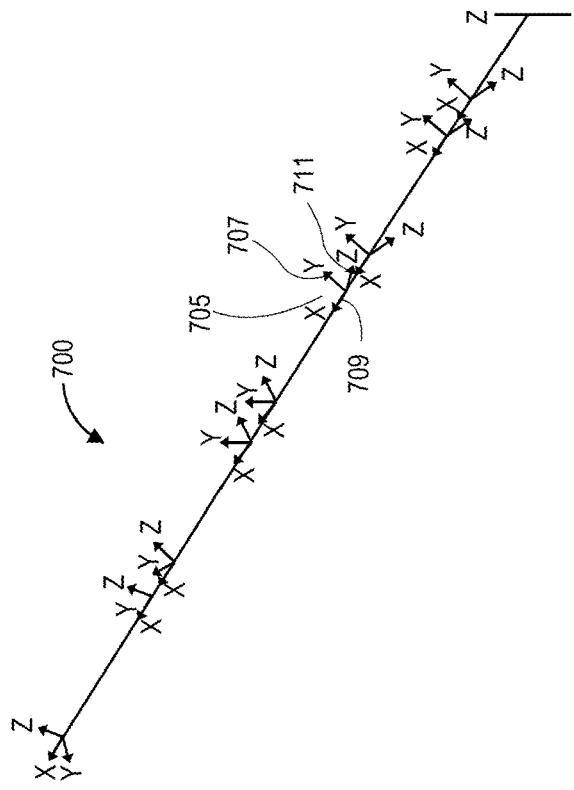
FIGS. 7A and 7B illustrate a rotation of frames of a framework about a first axis.
Figure 7B:
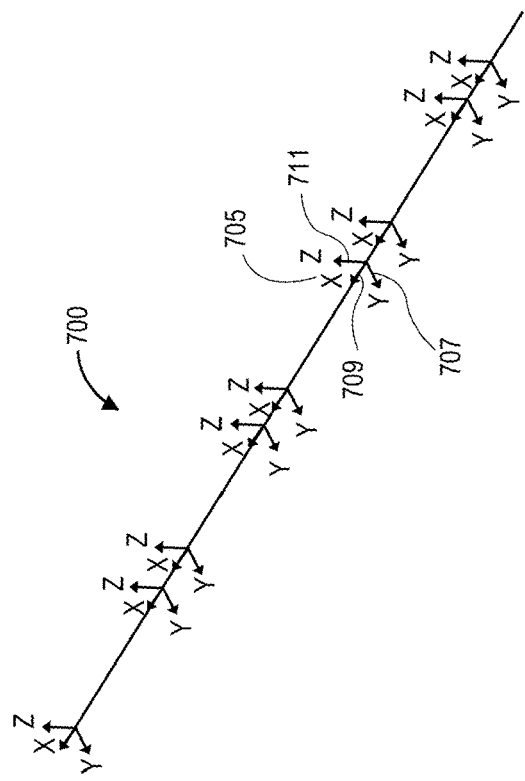

For example, FIGS. 7A and 7B illustrate a rotation of frames of a framework about a first axis. Rotation of the frames corresponds to a rotation/bend/manipulation to be applied to a corresponding 3-D object at particular locations. FIG. 7A illustrates an example of a framework 700 before a rotation is applied. FIG. 7B illustrates an example of the framework 700 after a rotation is applied to a group of the frames of the framework 700 about a first axis (e.g., the x-axis 709 as shown). For example, the frame 705 may be rotated around the x-axis 709, where the framework 700 along the x-axis 709 is not altered. In this example, the y-axis 707 and the z-axis 711 of frame 705 are rotated about the x-axis 709 to create a rotation in the framework 700. The rotation in the framework 700 may correspond to a rotation/bend/manipulation in a 3-D object at a particular location.

Figure 8:
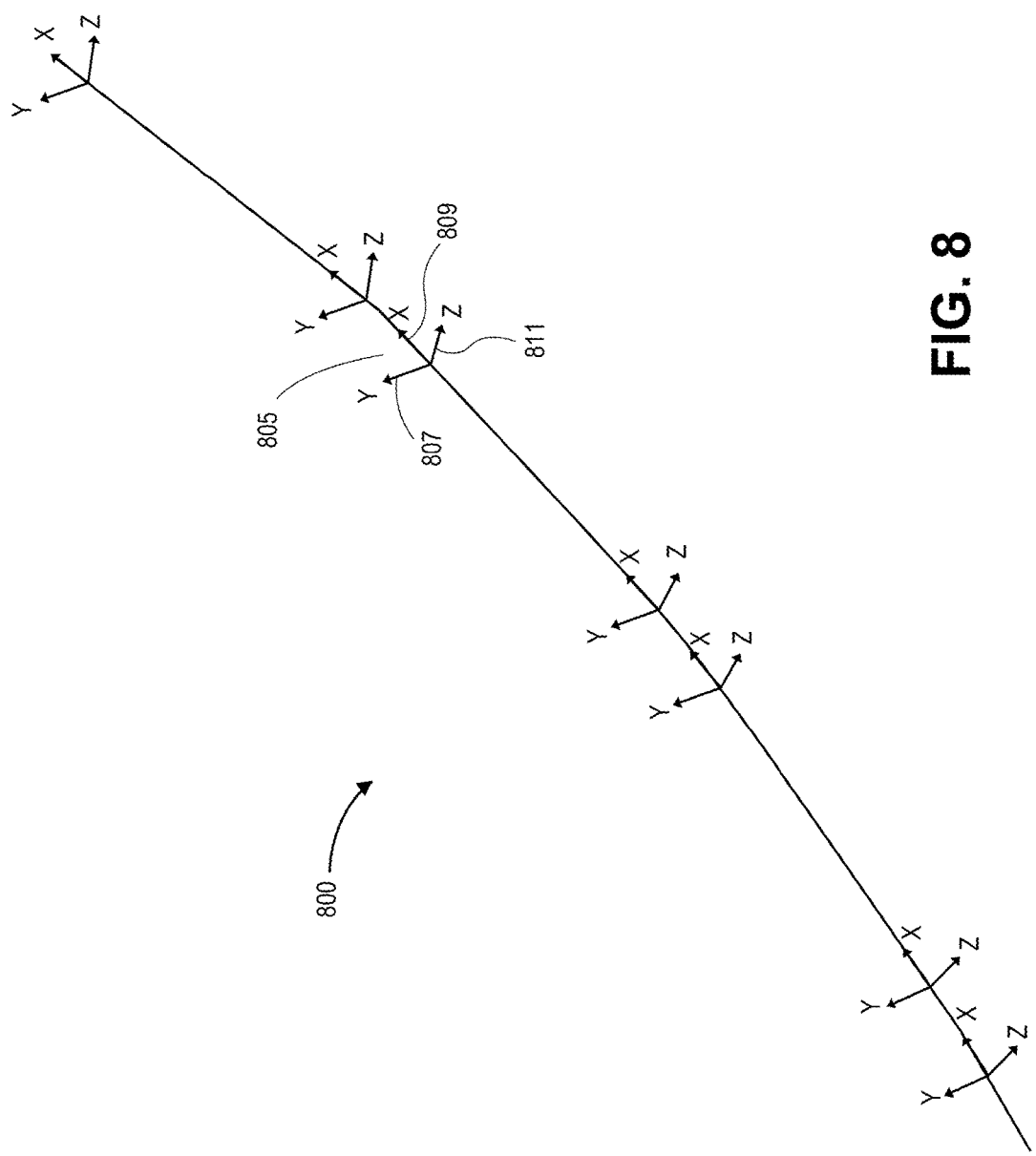
FIG. 8 illustrates a rotation of frames of a framework about a second axis.
Figure 9:
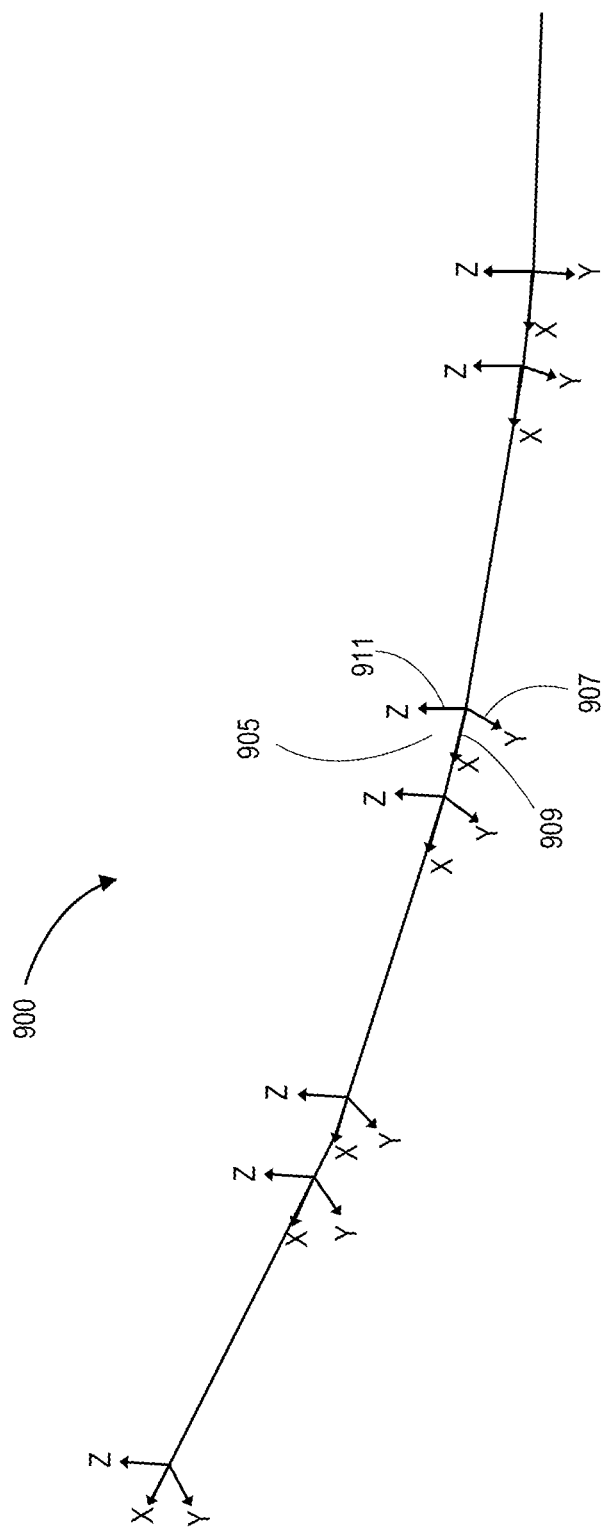
FIG. 9 illustrates a rotation of frames of a framework about a third axis.

Similarly, rotations may be applied to frames of the framework 700 about the other axes (e.g., the y-axis 707 and the z-axis 711). FIG. 8 illustrates an example of the framework 700 after a rotation is applied to a group of the frames of the framework 700 about a second axis (e.g., the y-axis 707 as shown). For example, the frame 705 may be rotated around the y-axis 707 so that the framework 700 along the y-axis 707 is not altered. Therefore, in this example, the x-axis 709 and the z-axis 711 of frame 705 are rotated about the y-axis 707 to create a rotation in the framework 700. FIG. 9 illustrates an example of the framework 700 after a rotation is applied to a group of the frames of the framework 700 about a third axis (e.g., the z-axis 711 as shown). For example, the frame 705 may be rotated around the z-axis 711, where the framework 700 along the z-axis 711 is not altered. In this example, the x-axis 709 and the y-axis 707 of frame 705 are rotated about the z-axis 711 to create a rotation in the framework 700. The rotation in the framework 700 in the x-, y-, and z-directions may correspond to a rotation/bend/manipulation in a 3-D object at a particular location. As would be understood by one of skill in the art, rotations about one or more axes of one or more frames may be applied to any given framework.

A digital representation of the 3-D object may be rendered based on the framework. For example, an initial digital representation of a 3-D object may be associated with an initial framework before applying any rotations to the frames of the framework. The digital representation of the initial 3-D object may be created using CAD/CAM or other appropriate software or techniques as would be understood by one of skill in the art. A framework may be generated for the 3-D object, either automatically or by a human and input into a computer. The location of frames in the framework may be based, for example, on certain parameters as discussed above (e.g., application and/or physical properties of the 3-D object). Further, in some embodiments, constraints/thresholds may also be defined for each of the frames as to a degree of rotating/bendg/manipulating that may be applied to a given frame based on certain parameters as discussed above (e.g., physical properties of the 3-D object). The process 300 of FIG. 3 may be used for manufacturing a 3-D object based on the digital representation of the 3-D object. The 3-D object may include a plate for use in surgery. For example, the plate may be used in cranio-maxillo facial surgery.

In some embodiments, a user of the computer 102a may apply rotations/bends/manipulations to one or more of the frames of the framework. Further, based on the rotated/bent/manipulated frames of the framework and the initial digital representation of the 3-D object, a revised or final representation of the 3-D object may be generated. For example, morphing techniques may be applied to the initial digital representation of the 3-D object based on the rotated/bent/manipulated frames of the framework to generate the revised or final representation of the 3-D object. The morphing techniques may include known morphing techniques in the art such as morphing algorithms including the Beier-Neely Morphing Algorithm and other morphing algorithms such as those used in software such as Abrosoft FantaMorph, Gryphon Software Morph, Morpheus, MorphThing.ADD.

In some embodiments, a user of the computer 102a may select a particular 3-D object and an application for the 3-D object (e.g., applying a plate to a jaw of a patient). For example, a database of objects (e.g., plates) and applications for the objects (e.g., surgery) may be maintained (e.g., on computer 102a or on a server) from which a user may make a selection. In response, a framework corresponding to the selected 3-D object may be automatically rotated/manipulated/bent according to the selected application. Based on the automatically rotated/bent/manipulated frames of the framework and an initial digital representation of the selected 3-D object, a revised or final representation of the 3-D object may be generated using, for example, morphing techniques as described above. In some embodiments, a user is able to determine exactly how much and in what direction an object has been rotated/manipulated/bent based on the framework before rotation and the framework after rotation.

In some embodiments, a model including a framework lying in two dimensional space may be achieved. A framework rotated, manipulated, or bent in two dimensional ("2-D") space may be referred to as an "in-plane" rotated manipulated/bent framework. A framework rotated, manipulated, or bent in three dimensional ("3-D") space may be referred to as an "out-of-plane" rotated/manipulated/bent framework. In-plane rotation/manipulation/bending may be achieved by removing an out-of-plane rotation of a framework, such as removing all rotations around a particular axis of the 3-D coordinates (x-axis, y-axis, or z-axis). For example, in-plane rotation/manipulation/bending may be achieved by removing rotations about a first axis direction by performing a first rotation about a first axis in the first axis direction for a first frame and performing a second rotation about a second axis in the first axis direction for a second frame. In some aspects, the degree of the second rotation may be based on the first rotation.

FIG. 10 illustrates an example of a process 1000 for achieving an in-plane rotated/manipulated/bent framework by removing a rotation/manipulation/bend along the framework about a y-axis. At block 1002, the process 1000 begins by identifying a frame within a framework. For example, the first frame in a framework may initially be identified. At block 1004, the process 1000 determines whether there is a rotation about the y-axis at the identified frame. At block 1006, if the process 1000 determines that there is no rotation about the y-axis, the process 1000 determines whether there are any further frames. If the process 1000 determines that there are further frames within the framework, the process 1000 identifies a next frame within the framework at block 1010 and determines whether there is a rotation about the y-axis in the next frame. If the process 1000 determines that there is a bend about the y-axis in any of the identified frames, the process 1000 removes the rotation about the y-axis at block 1008. As a result of the removal of the rotation about the y-axis at the identified frame, all previous frames will be rotated by the same amount as is required to remove the rotation about the y-axis in the currently identified frame. The process 1000 iteratively repeats until all frames have been identified and all rotations about the y-axis have been removed. At step 1006, if the process 1000 determines that there are not any further frames in the framework, indicating that all frames have been identified, the process 1000 ends. As would be understood by one of skill in the art, rotations about one or more axes of one or more frames may be removed from any given framework in order to achieve an in-plane rotated/manipulated/bent framework.

Figure 11:
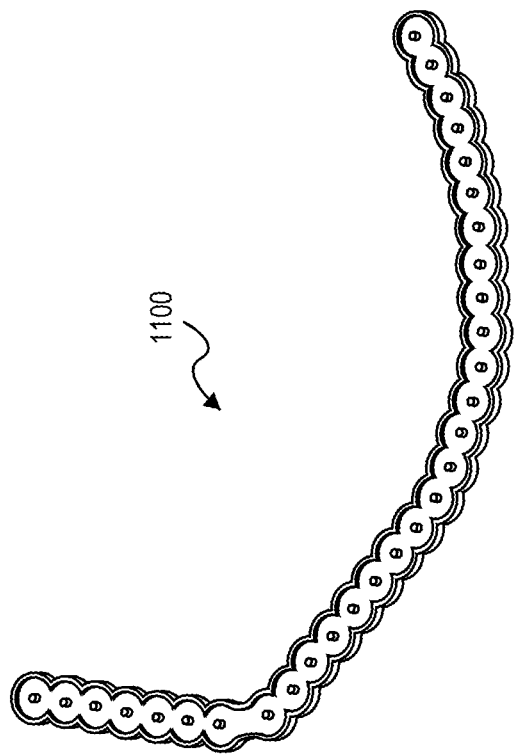
FIG. 11 illustrates an exemplary guide for use with a physical object.

FIG. 11 illustrates an exemplary guide 1100 for use with a physical object. For example, a printer may be configured to generate the guide 1100 for use with a plate based on the framework. A user may place the plate in the guide 1100 and manipulate the plate accordingly so that the plate is properly manipulated for the intended application. For example, if the plate is intended to be applied to a patient's ankle bone, the guide 1100 facilitates the proper bending of the plate so that the plate may fit properly upon the patient's ankle bone. The guide 1100 may be designed so that either an in-plane manipulated plate or an out-of-plane manipulated plate fits in the guide.

Figure 12:
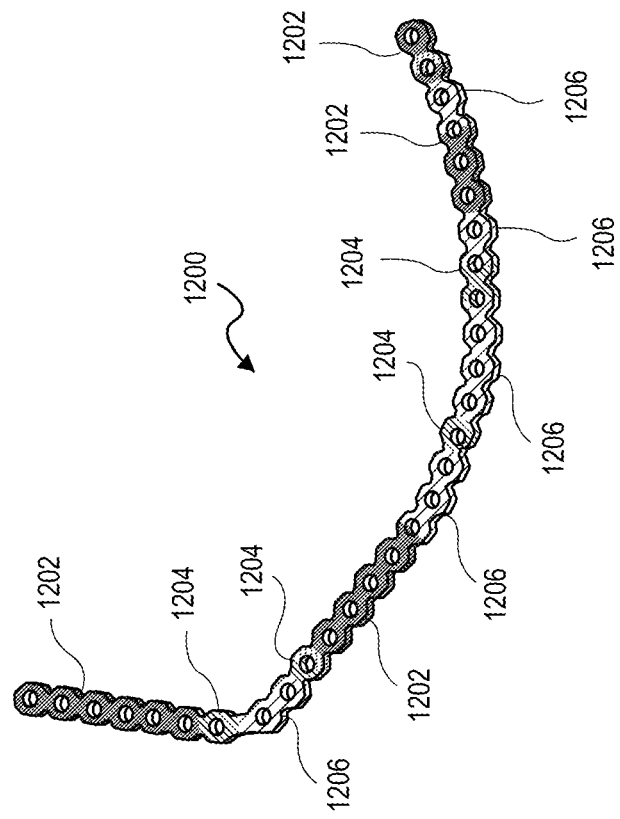
FIG. 12 illustrates an exemplary plate with color coded sections.

FIG. 12 illustrates an exemplary object 1200, such as a plate, with color coded sections. The plate may be generated or manufactured, for example, using the process 300 of FIG. 3 based on a digital representation of the plate using the plate's framework. In some embodiments, each different colored section provides an indication of how each section may be manipulated by a user. The color coding may be used to manipulate the plate in two dimensions or three dimensions. In an exemplary embodiment, color coded sections 1202 may be blue, and may indicate to the user that no manipulations may be made at these sections. Further, color coded sections 1204 may be red, and may indicate that only concave manipulations may be made to the plate in these sections. Further, color coded sections 1206 may be green, and may indicate to the user that only convex manipulations may be made to the plate in these sections. In some embodiments, each different colored section provides an indication of how an already manipulated plate has been manipulated, and may provide the user an indication of how further manipulations may be made. The color coded plate may be used in place of or in addition to the guide illustrated in FIG. 12. As would be understood by one of skill in the art, different colors and manipulations may be indicated by the color coded plate.

Figure 13:
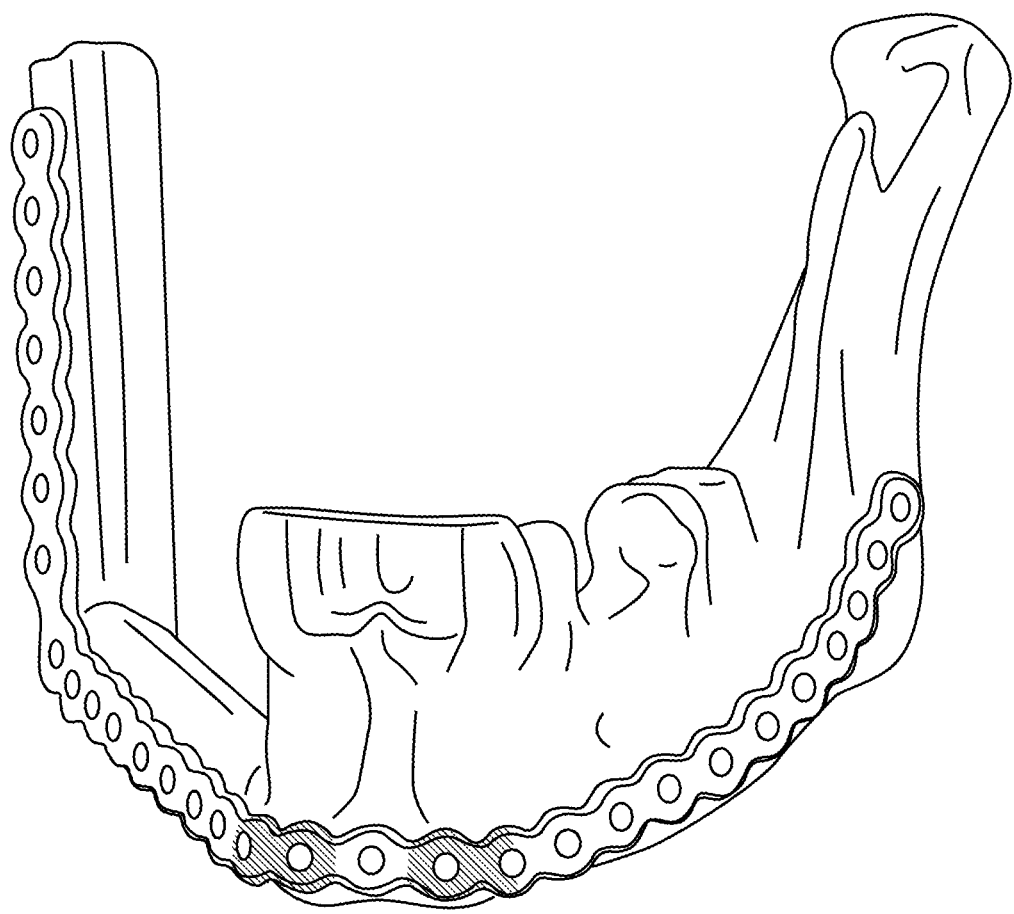
FIG. 13 illustrates an exemplary application of a generated physical object.

FIG. 13 illustrates an exemplary application of a generated physical object. In some embodiments, the physical object may include a plate for use in surgery. The plate may be two dimensional or three dimensional. For example, the plate may be three dimensional and may be used in cranio-maxillo facial surgery. In this example, the plate may be used by a surgeon to treat diseases, injuries, and defects in the face, head, neck, jawbones, and any other part of the oral and/or maxillofacial region. As illustrated in FIG. 13, the plate may be manipulated to fit the contour of a patient's jawbone. For example, a model of the plate may be generated based on the framework and the one or more constraints on manipulation of the frames. The process 300 of FIG. 3 may then be used for manufacturing the plate based on the model of the plate. In some embodiments, the plate may be manufactured in a manipulated state ready for use in the cranio-maxillo facial surgery. In the event the pre-manipulated plate does not fit the particular patient's jawbone, the surgeon may make incremental manipulations to the plate in order to form the plate to the patient's jaw. In some embodiments, the plate may be manufactured in a non-manipulated state, and a surgeon may manipulate the plate using a guide (e.g., the guide of FIG. 11) to form the plate to the patient's jaw. In some embodiments, the plate may be manufactured in a non-manipulated state with color coded sections (e.g., the color coded plate of FIG. 12), and a surgeon may manipulate the plate according to the color coded sections in order to form the plate to the patient's jaw. As would be understood by one of skill in the art, the physical object may be any type of physical object that can be manipulated. For example, the physical object may be an airplane wing or siding for a building that can be modeled using a framework and constraints.

Figure 14:
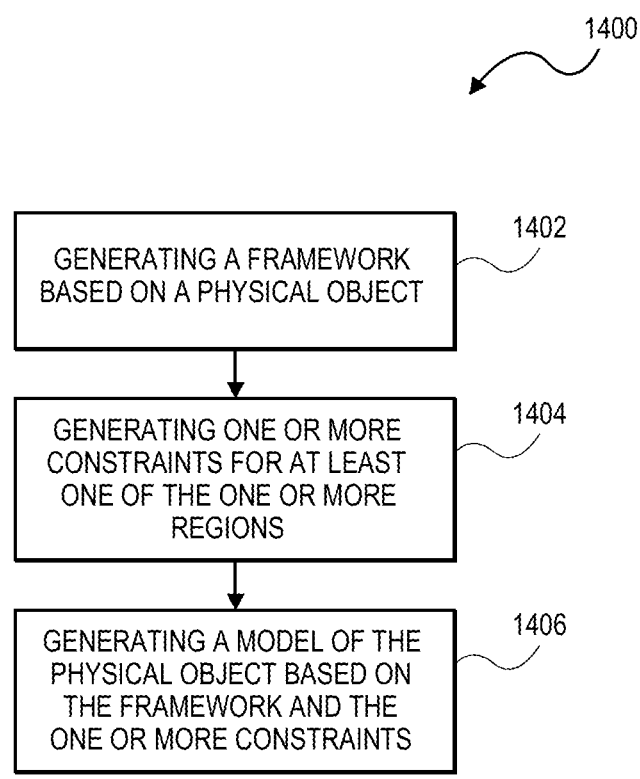
FIG. 14 illustrates a process for generating a model of a physical object based on a framework.

FIG. 14 illustrates an exemplary process for generating a model of a physical object based on a framework. For example, the process can be implemented as a method for generating a framework to guide manipulation of a physical object. At block 1402, the process generates a framework based on a physical object. The framework may comprise one or more frames that define one or more regions on the physical object for manipulation. The one or more frames may define one or more axes about which to rotate the framework and a degree to which to rotate the framework about the axes. At block 1404, the process generates one or more constraints for at least one of the one or more regions. The one or more constraints may comprise limitations on manipulations applied to the one or more regions based on physical properties of the physical object. For example, the constraints may limit how much the physical object can be manipulated at particular regions of the physical object. The constraints may prevent the physical object from being manipulated altogether at particular regions of the physical object. At block 1406, the process generates a model of the physical object based on the framework and the one or more constraints. The process may further include generating the actual physical object based on the model of the physical object, using, for example, the process 300 of FIG. 3. In some embodiments, the physical object is a plate that may be used for surgery (e.g., cranio-maxillo facial surgery), manufacture of an airplane, or any other process that uses manipulable objects. In some embodiments, the process may further include generating a guide for the plate based on the framework (e.g., the guide of FIG. 11). Further, the framework may include a one dimensional series of frames or a two dimensional grid of frames.

Figure 15:
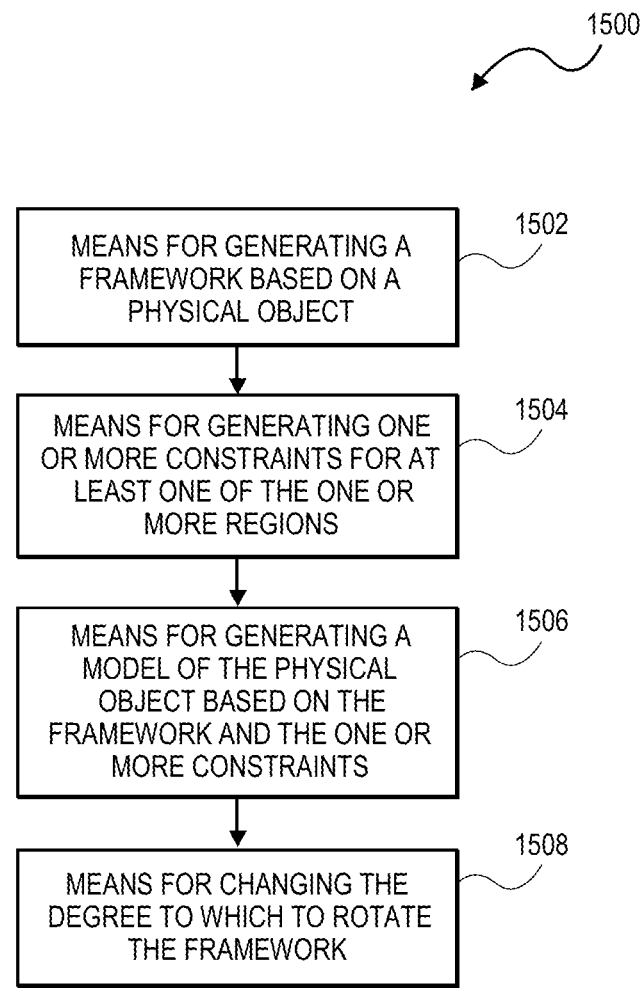
FIG. 15 illustrates an example of a functional block diagram of various components in a computing system.

FIG. 15 illustrates an example of a functional block diagram of various components in a computing system 1500, such as a processor that may be employed within the computer 102a of FIG. 1 or 2. Those skilled in the art will appreciate that the computing system may have more components than the simplified computing system 1500 shown in FIG. 15. The computing system 1500 shown includes only those components useful for describing some prominent features of implementations within the scope of the claims. The computing system 1500 comprises means 1502 for generating a framework based on a physical object. The framework may comprise one or more frames that define one or more regions on the physical object for manipulation. Further, each of the one or more frames may define one or more axes about which to rotate the framework and a degree to which to rotate the framework about the axes. The computing system 1500 further comprises means 1504 for generating one or more constraints for at least one of the one or more regions. The computing system 1500 further comprises means 1506 for generating a model of the physical object based on the framework and the one or more constraints. The computing system 1500 further comprises means 1508 for changing the degree to which to rotate the framework.

The means 1502 for generating a framework based on a physical object may be configured to perform one or more of the functions discussed above with respect to block 1402 illustrated in FIG. 14. The means 1502 for generating a framework based on a physical object may correspond to one or more modules, such as the processor 210, the output device 240, the network interface card 260, and the memory 220, discussed above with respect to FIG. 2. In some embodiments, the means 1502 for generating a framework may correspond to one or more modules included in the processor 210. The means 1504 for generating one or more constraints for at least one of the one or more regions may be configured to perform one or more of the functions discussed above with respect to block 1404 illustrated in FIG. 14. The means 1504 for generating one or more constraints may correspond to one or more modules, such as the processor 210, the output device 240, the network interface card 260, and the memory 220, discussed above with respect to FIG. 2. In some embodiments, the means 104 for generating one or more constraints may correspond to one or more modules included in the processor 210. The means 1506 for generating a model of the physical object based on the framework and the one or more constraints may be configured to perform one or more of the functions discussed above with respect to block 1406 illustrated in FIG. 14. The means 1506 for generating a model of the physical object may correspond to one or more modules, such as the processor 210, the output device 240, the network interface card 260, and the memory 220, discussed above with respect to FIG. 2. In some embodiments, the means 1506 for generating a model of the physical object may correspond to one or more modules included in the processor 210. The means 1508 for changing the degree to which to rotate the framework may correspond to one or more modules, such as the processor 210, the output device 240, the network interface card 260, and the memory 220, discussed above with respect to FIG. 2. In some embodiments, the means 1508 for changing the degree to which to rotate the framework may correspond to one or more modules included in the processor 210.

As used herein, an input device can be, for example, a keyboard, rollerball, mouse, voice recognition system or other device capable of transmitting information from a user to a computer. The input device can also be a touch screen associated with the display, in which case the user responds to prompts on the display by touching the screen. The user may enter textual information through the input device such as the keyboard or the touchscreen.

The invention is operational with numerous other general purpose or special purpose computing system environments or configurations. Examples of well-known computing systems, environments, and/or configurations that may be suitable for use with the invention include, but are not limited to, personal computers, server computers, hand-held or laptop devices, multiprocessor systems, microprocessor-based systems, programmable consumer electronics, network PCs, minicomputers, mainframe computers, distributed computing environments that include any of the above systems or devices, and the like.

As used herein, instructions refer to computer-implemented steps for processing information in the system. Instructions can be implemented in software, firmware or hardware and include any type of programmed step undertaken by components of the system.

A microprocessor may be any conventional general purpose single- or multi-chip microprocessor such as a Pentium® processor, a Pentium® Pro processor, a 8051 processor, a MIPS® processor, a Power PC® processor, or an Alpha® processor. In addition, the microprocessor may be any conventional special purpose microprocessor such as a digital signal processor or a graphics processor. The microprocessor typically has conventional address lines, conventional data lines, and one or more conventional control lines.

The system is comprised of various modules as discussed in detail. As can be appreciated by one of ordinary skill in the art, each of the modules may comprise various hardware components, sub-routines, procedures, definitional statements, and macros. Each of the modules may be separately compiled and linked into a single executable program and the description of each of these modules is used for convenience to describe the functionality of the preferred system. Thus, any processes that are undergone by each of the modules may be arbitrarily redistributed to one of the other modules, combined together in a single module, or made available in, for example, a shareable dynamic link library.

The system may be used in connection with various operating systems such as Linux®, UNIX® or Microsoft Windows®.

The system may be written in any conventional programming language such as C, C++, BASIC, Pascal, or Java, and ran under a conventional operating system. C, C++, BASIC, Pascal, Java, and FORTRAN are industry standard programming languages for which many commercial compilers can be used to create executable code. The system may also be written using interpreted languages such as Perl, Python or Ruby.

A web browser comprising a web browser user interface may be used to display information (such as textual and graphical information) to a user. The web browser may comprise any type of visual display capable of displaying information received via a network. Examples of web browsers include Microsoft's Internet Explorer browser, Netscape's Navigator browser, Mozilla's Firefox browser, PalmSource's Web Browser, Apple's Safari, or any other browsing or other application software capable of communicating with a network.

The invention disclosed herein may be implemented as a method, apparatus or article of manufacture using standard programming or engineering techniques to produce software, firmware, hardware, or any combination thereof. The term "article of manufacture" as used herein refers to code or logic implemented in hardware or non-transitory computer readable media such as optical storage devices, and volatile or nonvolatile memory devices or transitory computer readable media such as signals, carrier waves, etc. Such hardware may include, but is not limited to, field programmable gate arrays (FPGAs), application-specific integrated circuits (ASICs), complex programmable logic devices (CPLDs), programmable logic arrays (PLAs), microprocessors, or other similar processing devices.

What is claimed is:

1. An apparatus for generating a framework to guide manipulation of a physical object, the apparatus comprising:
a processor configured to:
generate an initial framework based on a physical object, the initial framework being associated with a digital representation of the physical object and comprising one or more frames that define one or more regions on the physical object for manipulation, wherein each of the one or more frames define one or more axes about which to rotate the initial framework and a degree to which to rotate the initial framework about the axes;
determine one or more constraints for at least one of the one or more regions, the one or more constraints comprising limitations on manipulations applied to the one or more regions based on physical properties of the physical object itself and not based on spatial relationships to other objects, wherein a threshold is defined for the at least one or more regions, the threshold indicating a degree of manipulating that may be applied to the corresponding frame;
generate a digital 3-D model of the physical object based on the initial framework and the one or more constraints by adjusting the initial framework at the one or more frames by bending, rotating, or manipulating the one or more frames in accordance with the limitations and the threshold; and
control generation of the physical object based on the digital 3-D model using an additive manufacturing apparatus.

2. The apparatus of claim 1, wherein the processor is configured to change the degree to which to rotate the initial framework based on a model of another physical object so the model of the physical object aligns with the model of the other physical object.

3. The apparatus of claim 1, wherein the processor is configured to generate another framework based on the generated initial framework by: removing rotations about a first axis direction of the generated initial framework by performing a first rotation about a first axis in the first axis direction for a first frame and performing a second rotation about a second axis in the first axis direction for a second frame, a degree of the second rotation being based on the first rotation.

4. The apparatus of claim 1, further comprising the additive manufacturing apparatus.

5. The apparatus of claim 1, wherein the physical object comprises a plate used for cranio-maxillo facial surgery.

6. The apparatus of claim 1, wherein the physical properties comprise one or more of the following: a material of the physical object and a shape of the physical object.

7. The apparatus of claim 1, wherein the physical properties comprise the material of the physical object.

8. The apparatus of claim 1, wherein the initial framework comprises at least one of a one dimensional series of frames and a two dimensional grid of frames.

9. The apparatus of claim 1, wherein the location of the one or more regions is based on the physical properties of the physical object.

10. A method of generating a framework to guide manipulation of a physical object, comprising:
generating an initial framework based on a physical object, the initial framework being associated with a digital representation of the physical object and comprising one or more frames that define one or more regions on the physical object for manipulation, wherein each of the one or more frames define one or more axes about which to rotate the initial framework and a degree to which to rotate the initial framework about the axes;
determining one or more constraints for at least one of the one or more regions, the one or more constraints comprising limitations on manipulations applied to the one or more regions based on physical properties of the physical object itself and not based on spatial relationships to other objects, wherein a threshold is defined for the at least one or more regions, the threshold indicating a degree of manipulating that may be applied to the corresponding frame;
generating a digital 3-D model of the physical object based on the initial framework and the one or more constraints by adjusting the initial framework at the one or more frames by bending, rotating, or manipulating the one or more frames in accordance with the limitations and the threshold; and
controlling generation of the physical object based on the digital 3-D model using an additive manufacturing apparatus.

11. The method of claim 10, further comprising changing the degree to which to rotate the initial framework based on a model of another physical object so the model of the physical object aligns with the model of the other physical object.

12. The method of claim 10, further comprising generating another framework based on the generated initial framework by:
removing rotations about a first axis direction of the generated initial framework by performing a first rotation about a first axis in the first axis direction for a first frame and performing a second rotation about a second axis in the first axis direction for a second frame, a degree of the second rotation being based on the first rotation.

13. The method of claim 10, wherein the physical properties comprise one or more of the following: a material of the physical object and a shape of the physical object.

14. The method of claim 10, wherein the physical properties comprise the material of the physical object.

15. The method of claim 10, wherein the initial framework comprises at least one of a one dimensional series of frames and a two dimensional grid of frames.

16. The method of claim 10, wherein the location of the one or more regions is based on the physical properties of the physical object.

17. An apparatus for generating a framework to guide manipulation of a physical object, the apparatus comprising:
means for generating an initial framework based on a physical object, the initial framework being associated with a digital representation of the physical object and comprising one or more frames that define one or more regions on the physical object for manipulation, wherein each of the one or more frames define one or more axes about which to rotate the initial framework and a degree to which to rotate the initial framework about the axes;

means for determining one or more constraints for at least one of the one or more regions, the one or more constraints comprising limitations or manipulations applied to the one or more regions based on physical properties of the physical object itself and not based on spatial relationships to other objects, wherein a threshold is defined for the at least one or more regions, the threshold indicating a degree of manipulating that may be applied to the corresponding frame; and means for generating a digital 3-D model of the physical object based on the initial framework and the one or more constraints by adjusting the initial framework at the one or more frames by bending, rotating, or manipulating the one or more frames in accordance with the limitations and the threshold; and means for controlling generation of the physical object based on the digital 3-D model using an additive manufacturing apparatus.

18. The apparatus of claim 17, wherein the means for generating an initial framework is configured to generate another framework based on the generated framework by:
removing rotations about a first axis direction of the generated initial framework by performing a first rotation about a first axis in the first axis direction for a first frame and performing a second rotation about a second axis in the first axis direction for a second frame, a degree of the second rotation being based on the first rotation.

19. The apparatus of claim 1, further wherein the processor is further configured to generate a digital 3-D model of a guide for use with the physical object based on the initial framework, wherein the guide is configured to receive the physical object and direct manipulations of the physical object.

20. The apparatus of claim 1, wherein the one or more constraints further comprise limitations on manipulations applied to the one or more regions based on spatial relationships to other objects.

\* \* \* \* \*